(12) United States Patent
Chin et al.

(10) Patent No.: US 8,372,118 B2
(45) Date of Patent: Feb. 12, 2013

(54) SPINOUS PROCESS FIXATION IMPLANT

(75) Inventors: Kingsley R. Chin, Riviera Beach, FL (US); Christine Reif, Ipswich, MA (US); Ernie Corrao, Bethel, CT (US); Todd Saunders, Boston, MA (US)

(73) Assignee: Spinefrontier Inc, Beverly, MA (US)

( * ) Notice: Subject to any disclaimer, the term of this patent is extended or adjusted under 35 U.S.C. 154(b) by 496 days.

(21) Appl. No.: 12/635,811

(22) Filed: Dec. 11, 2009

(65) Prior Publication Data

US 2010/0087860 A1    Apr. 8, 2010

Related U.S. Application Data

(63) Continuation-in-part of application No. 11/609,418, filed on Dec. 12, 2006.

(51) Int. Cl.
*A61B 17/70* (2006.01)
(52) U.S. Cl. ......................... 606/249; 606/279
(58) Field of Classification Search .................. 606/248, 606/249
See application file for complete search history.

(56) References Cited

U.S. PATENT DOCUMENTS

| | | | |
|---|---|---|---|
| 5,496,318 A | 3/1996 | Howland et al. | |
| 6,652,527 B2 * | 11/2003 | Zucherman et al. | 606/249 |
| 7,749,252 B2 * | 7/2010 | Zucherman et al. | 606/248 |
| 7,753,938 B2 * | 7/2010 | Aschmann et al. | 606/248 |
| 7,955,392 B2 * | 6/2011 | Dewey et al. | 623/17.16 |
| 2002/0091446 A1 | 7/2002 | Zucherman et al. | |
| 2003/0040746 A1 * | 2/2003 | Mitchell et al. | 606/61 |
| 2004/0106995 A1 * | 6/2004 | Le Couedic et al. | 623/17.11 |
| 2005/0102028 A1 | 5/2005 | Arnin et al. | |
| 2005/0245937 A1 * | 11/2005 | Winslow | 606/90 |
| 2005/0267579 A1 | 12/2005 | Reiley et al. | |
| 2006/0247640 A1 | 11/2006 | Blackwell et al. | |
| 2007/0093825 A1 * | 4/2007 | Ferree et al. | 606/61 |
| 2007/0106385 A1 | 5/2007 | Zucherman et al. | |
| 2008/0058941 A1 | 3/2008 | Zucherman et al. | |
| 2008/0108990 A1 | 5/2008 | Mitchell et al. | |
| 2008/0108993 A1 | 5/2008 | Bennett et al. | |
| 2008/0154307 A1 | 6/2008 | Colleran et al. | |
| 2008/0161818 A1 | 7/2008 | Kloss et al. | |
| 2008/0167656 A1 | 7/2008 | Zucherman et al. | |
| 2008/0177391 A1 * | 7/2008 | Mitchell et al. | 623/17.16 |
| 2008/0183211 A1 * | 7/2008 | Lamborne et al. | 606/249 |
| 2010/0036419 A1 * | 2/2010 | Patel et al. | 606/249 |

* cited by examiner

*Primary Examiner* — Eduardo C Robert
*Assistant Examiner* — Jerry Cumberledge
(74) *Attorney, Agent, or Firm* — AKC Patents LLC; Aliki K. Collins

(57) ABSTRACT

An implantable spinous process fixation device includes an elongated component, top and bottom pivoting wing components, arranged opposite and parallel to the elongated component and separated from it by a spacer. First and second spinous processes of first and second adjacent vertebras are clamped between a top portion of the elongated component and the top pivoting wing and between a bottom portion of the elongated component and the bottom pivoting wing, respectively, by pivoting the top and bottom pivoting wings toward the top and bottom portions of the elongated component. The clamping of the spinous processes stabilizes the positions of the adjacent vertebras and prevents them from moving relative to each other.

17 Claims, 22 Drawing Sheets

SPINOUS PROCESS FIXATION IMPLANT

CROSS REFERENCE TO RELATED CO-PENDING APPLICATIONS

This application claims the benefit of U.S. provisional application Ser. No. 61/121,955 filed Dec. 12, 2008 and entitled "IMPROVED SPINOUS PROCESS FIXATION IMPLANT", the contents of which are expressly incorporated herein by reference.

This application is also a continuation in part of U.S. utility application Ser. No. 11/609,418 filed Dec. 12, 2006 and entitled "SPINOUS PROCESS FIXATION IMPLANT", the contents of which are expressly incorporated herein by reference.

FIELD OF THE INVENTION

The present invention relates to a system and a method for spinal stabilization through an implant, and more particularly to spinal stabilization through attachment of an improved implant to the spinous processes along one or more vertebras.

BACKGROUND OF THE INVENTION

The human spine comprises individual vertebras 30 (segments) that are connected to each other to form a spinal column 29, shown in FIG. 1. Referring to FIGS. 1B and 1C, each vertebra 30 has a cylindrical bony body (vertebral body) 32, three winglike projections (two transverse processes 33, 35 and one spinous process 34), left and right facet joints 46, lamina 47, left and right pedicles 48 and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements. The vertebras 30 are separated and cushioned by thin pads of tough, resilient fiber known as inter-vertebral discs 40. Disorders of the spine occur when one or more of the individual vertebras 30 and/or the inter-vertebral discs 40 become abnormal either as a result of disease or injury. In these pathologic circumstances, fusion of adjacent vertebral segments may be tried to restore the function of the spine to normal, achieve stability, protect the neural structures, or to relief the patient of discomfort.

Several spinal fixation systems exist for stabilizing the spine so that bony fusion is achieved. The majority of these fixation systems utilize rods that attach to screws threaded into the vertebral bodies or the pedicles 48, shown in FIG. 3C. In some cases component fixation systems are also used to fuse two adjacent vertebral segments. This construction usually consists of two longitudinal components that are each placed laterally to connect two adjacent pedicles of the segments to be fused. This system can be extended along the sides of the spine by connecting two adjacent pedicles at a time similar to the concept of a bicycle chain. Current component fixation systems are basically designed to function in place of rods with the advantage of allowing intersegmental fixation without the need to contour a long rod across multiple segments. Both the plating systems and the rod systems add bulk along the lateral aspect of the spine limits access to the pars and transverse processes for decortication and placement of bone graft. In order to avoid this limitation many surgeons decorticate before placing the rods, thereby increasing the amount of blood loss and making it more difficult to maintain a clear operative field. Placing rods or components lateral to the spine leaves the center of the spinal canal that contains the dura, spinal cords and nerves completely exposed. In situations where problems develop at the junction above or below the fused segments necessitating additional fusion, the rod fixation system is difficult to extend to higher or lower levels that need to be fused. Although there are connectors and techniques to lengthen the fixation, they tend to be difficult to use and time consuming.

Accordingly, there is a need for a spinal stabilization device that does not add bulk to the lateral aspect of the spine and does not limit access to the pars and transverse processes for decortication and placement of bone graft.

SUMMARY OF THE INVENTION

In general, in one aspect, the invention features an implantable assembly for stabilization of two adjacent spinous processes in a spinal column, including an elongated component extending along a first axis, a first pivoting wing, a second pivoting wing and a spacer extending along a second axis. The second axis is perpendicular to the first axis and the spacer is placed between the elongated component and the first and second pivoting wings. The first and second pivoting wings are arranged opposite to the elongated component at a distance defined by the spacer width and comprise inner surfaces that face an inner surface of the elongated component. The first and second pivoting wings pivot around a third axis, which is perpendicular to the first axis and the second axis. A first spinous process is placed and clamped between the first pivoting wing inner surface and a first area of the elongated component inner surface by pivoting the first pivoting wing toward the elongated component. A second spinous process is placed and clamped between the second pivoting wing inner surface and a second area of the elongated component inner surface by pivoting the second pivoting wing toward the elongated component.

Implementations of this aspect of the invention may include one or more of the following features. The assembly further includes first and second pins. The first pin is dimensioned to pass through three concentrically aligned through-bore openings formed in the first pivoting wing, the first spinous process and the first area of the elongated component, respectively. The second pin is dimensioned to pass through three concentrically aligned through-bore openings formed in the second pivoting wing, the second spinous process and the second area of the elongated component, respectively. The first and second areas of the elongated component inner surface and the first and second wing inner surfaces comprise protrusions designed to frictionally attach to surfaces of the first and second spinous processes, respectively. The assembly further includes a third pin dimensioned to pass through two concentrically aligned through-bore openings formed in the spacer along the second axis and in the center of the elongate component, respectively. The third pin comprises a ring extending from a first end and the ring defines a through opening extending along the third axis. Each of the pivoting wings comprises a ring extending from a first end of each pivoting wing and the pivoting wing rings are oriented concentric with the third pin ring along the third axis. The assembly may further include an elongated bolt dimensioned to pass through the pivoting wing rings and the third pin ring. The elongated bolt comprises threads formed at a portion of the bolt, and the threads are dimensioned to engage a nut after the bolt exits the rings. The third pin ring comprises radially extending grooves that interlock with radially extending grooves formed in the pivoting wing rings. The spacer is dimensioned to fit between the first and second spinous processes and comprises an outer surface that is sculpted to conform to the shape of the spinous processes. The assembly may further include first, second and third locking elements for securing the first, second and third pins, respectively, to the elongated component. The locking elements comprise a setscrew dimensioned to engage threads formed in openings formed in the elongated component, and the openings extend along an axis perpendicular to the first and second axes. The spacer comprises fenestrations configured to receive bone growth promoting material. The spacer may be an integral extension of the elongated component.

In general, in another aspect, the invention features a method for stabilizing two adjacent spinous processes in a spinal column including the following. Providing an elongated component extending along a first axis. Providing first and second pivoting wings. Providing a spacer extending along a second axis, wherein the second axis is perpendicular to the first axis. Placing the spacer between the elongated component and the first and second pivoting wings. Arranging the first and second pivoting wings opposite to the elongated component and placing them at a distance defined by the spacer width so that inner surfaces of the pivoting wings face an inner surface of the elongated component. Pivoting the first and second pivoting wings around a third axis, which is perpendicular to the first axis and the second axis. Placing a first spinous process and clamping it between the first pivoting wing inner surface and a first area of the elongated component inner surface. Placing a second spinous process and clamping it between the second pivoting wing inner surface and a second area of the elongated component inner surface.

Among the advantages of this invention may be one or more of the following. The assembly stabilizes vertebras by attaching components to the spinous processes of the vertebras. This stabilization device does not add bulk to the lateral aspect of the spine and does not limit access to the pars and transverse processes for decortication and placement of bone graft. The compact form of the implant assembly allows it to be implanted via mini-open surgery. The device form conforms to the local vertebral anatomy. In particular, the adjustable winged plates fit to the spinous process contour. The device may be used alone or as adjunct to facet or pedicle screw systems. It provides multi-level (i.e., multi-vertebra) fusion through replication of the basic unit. The device is securely attached to the spinous processes via the center post, individual wings and pins. The fenestrated spacer enables application of graft material and promotes bone growth through the device.

The details of one or more embodiments of the invention are set forth in the accompanying drawings and description below. Other features, objects and advantages of the invention will be apparent from the following description of the preferred embodiments, the drawings and from the claims

BRIEF DESCRIPTION OF THE DRAWINGS

Referring to the figures, wherein like numerals represent like parts throughout the several views:

FIG. 1A is a side view of the human spinal column;
FIG. 1B is an enlarged view of area A of FIG. 1A.

DETAILED DESCRIPTION OF THE INVENTION

The present invention relates to a system and a method for an improved spinous process fixation implant.

Figure 1C:
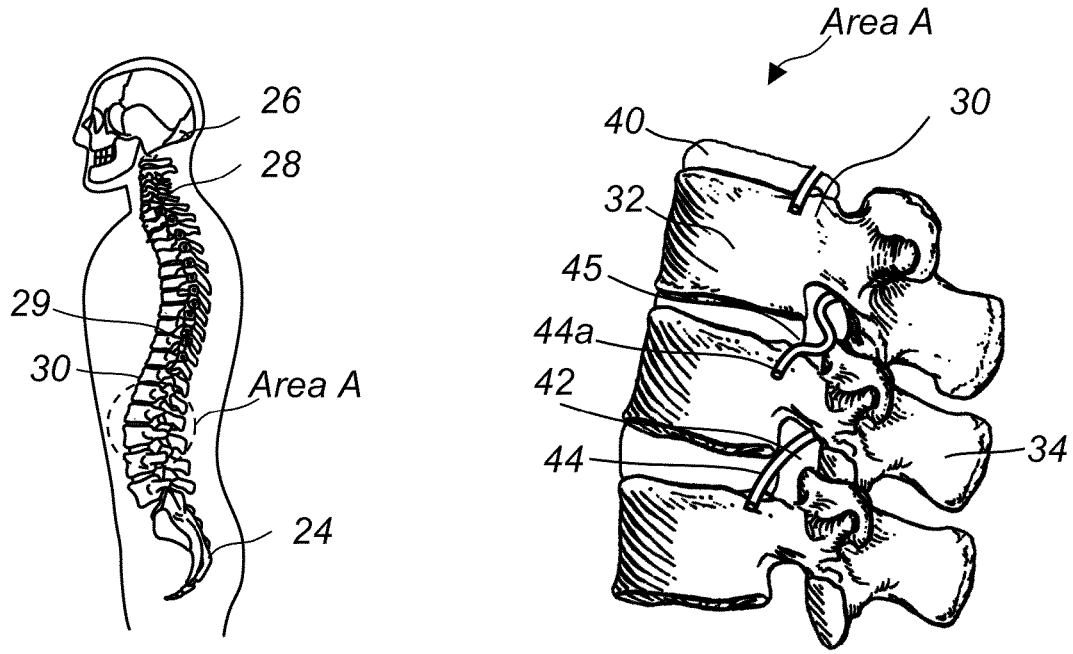
FIG. 1C is an axial cross-sectional view of a lumbar vertebra.
Figure 1C:
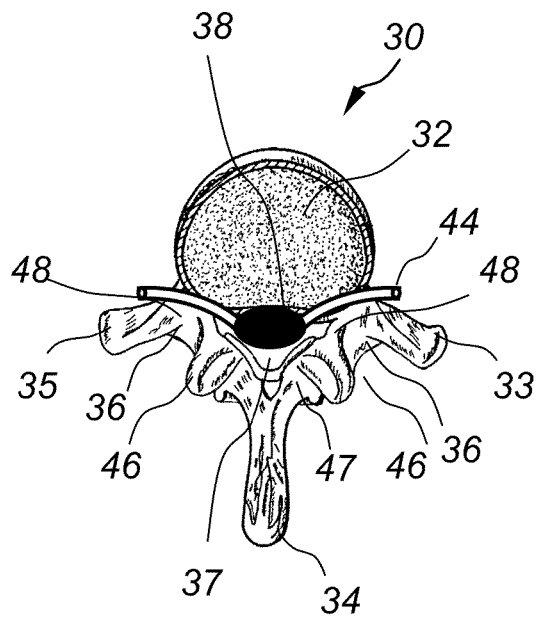
Figure 2:
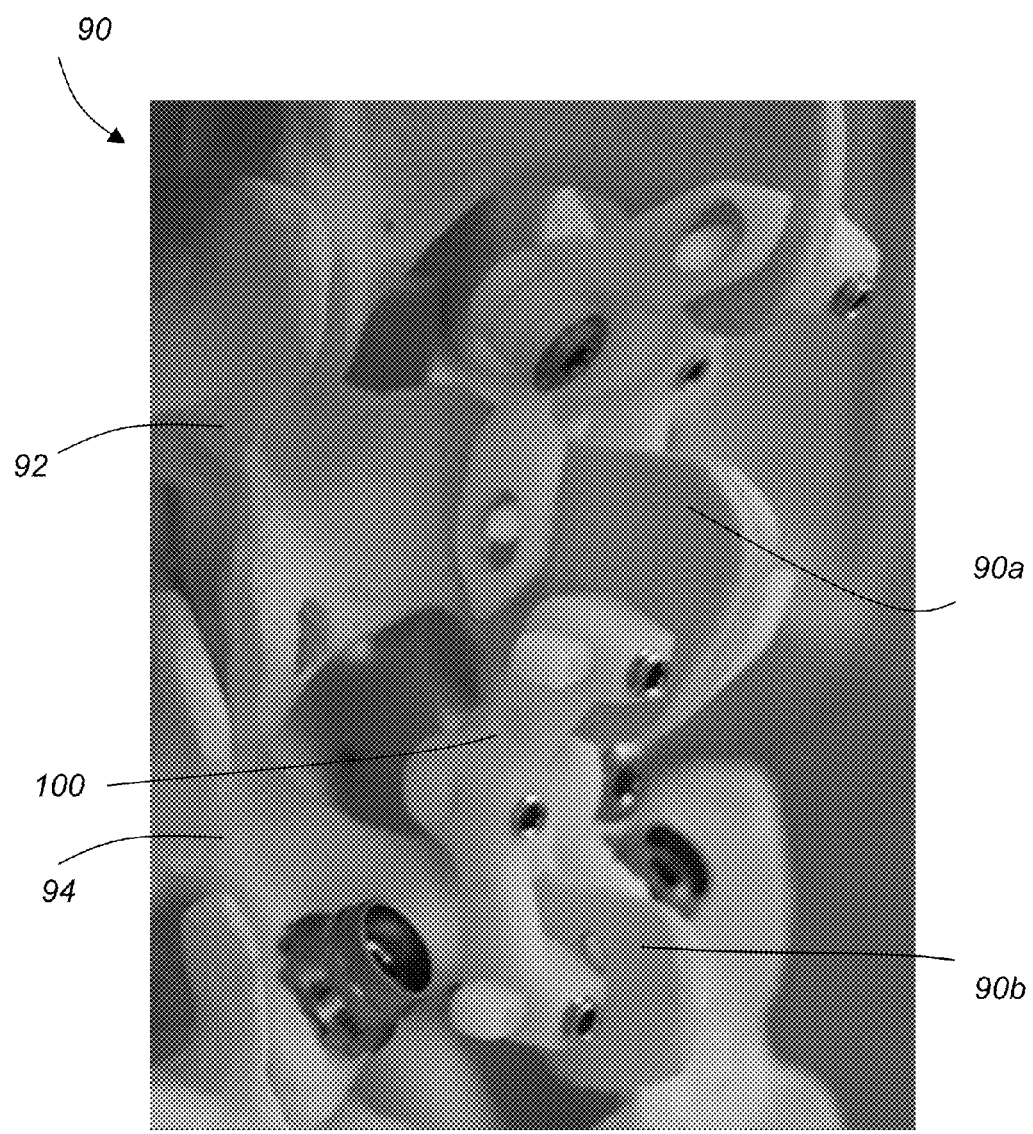
FIG. 2 is a posterior view of a portion of the spine with a first embodiment of a spinous process fixation implant according to the present invention affixed thereto.
Figure 3:
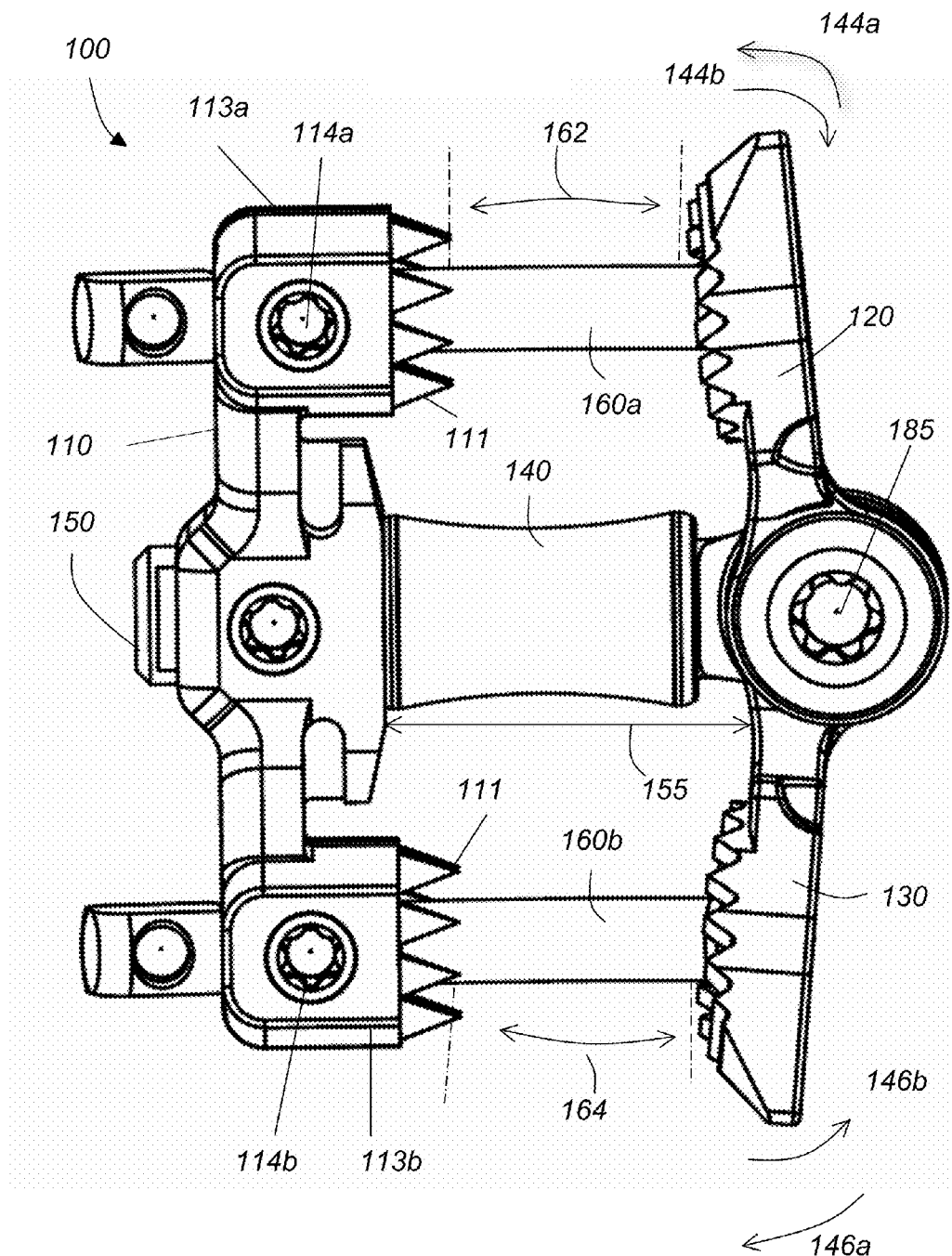
FIG. 3 is a front view of the spinous process fixation implant of FIG. 2.
Figure 4:
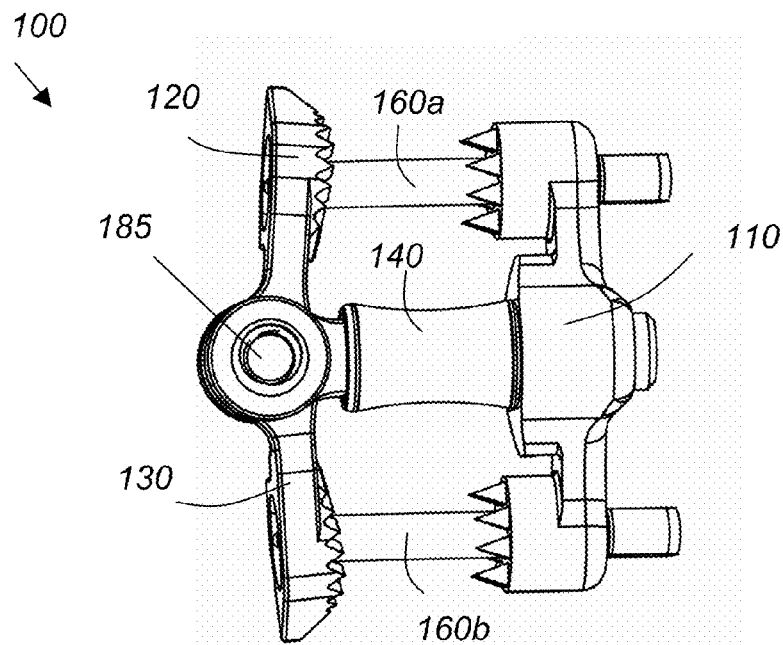
FIG. 4 is a back view of the spinous process fixation implant of FIG. 2.

Referring to FIG. 2, spinous process fixation assembly 100 stabilizes two adjacent vertebras 92, 94 of the human spine by engaging and locking their spinous processes 90a and 90b, respectively. Referring to FIG. 3, spinous process fixation assembly 100 includes an elongate component 110, top and a bottom pivoting wing components 120, 130 and a spacer 140. Top and bottom pivoting wing components 120, 130 are arranged opposite to component 110 at a distance 155 set by the length of spacer 140. Top and bottom pivoting wing components 120, 130 pivot around axis 180 (shown in FIG. 6) independent from each other, forming angles 162, 164 with component 110, respectively. The pivoting motion of components 120, 130 along directions 144a, 144b and 146a, 146b, moves them close to or away from the elongated component 110, as shown in FIG. 3 and results in clamping or unclamping of the spinous processes 90a, 90b between the elongated component 110 and pivoting wing components 120 and 130, respectively. The clamping of the spinous processes 90a, 90b stabilizes the positions of the corresponding vertebras 92, 94 and prevents them from moving relative to each other.

Figure 5A:
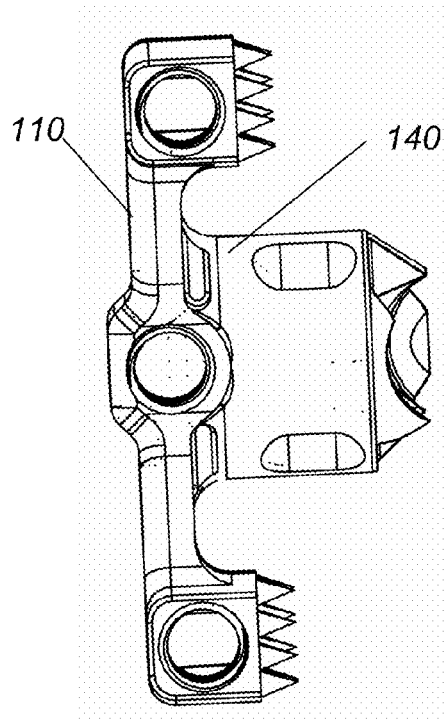
FIG. 5A is a front view of another embodiment of the elongated component 110 with the integrated spacer 140.
Figure 5:
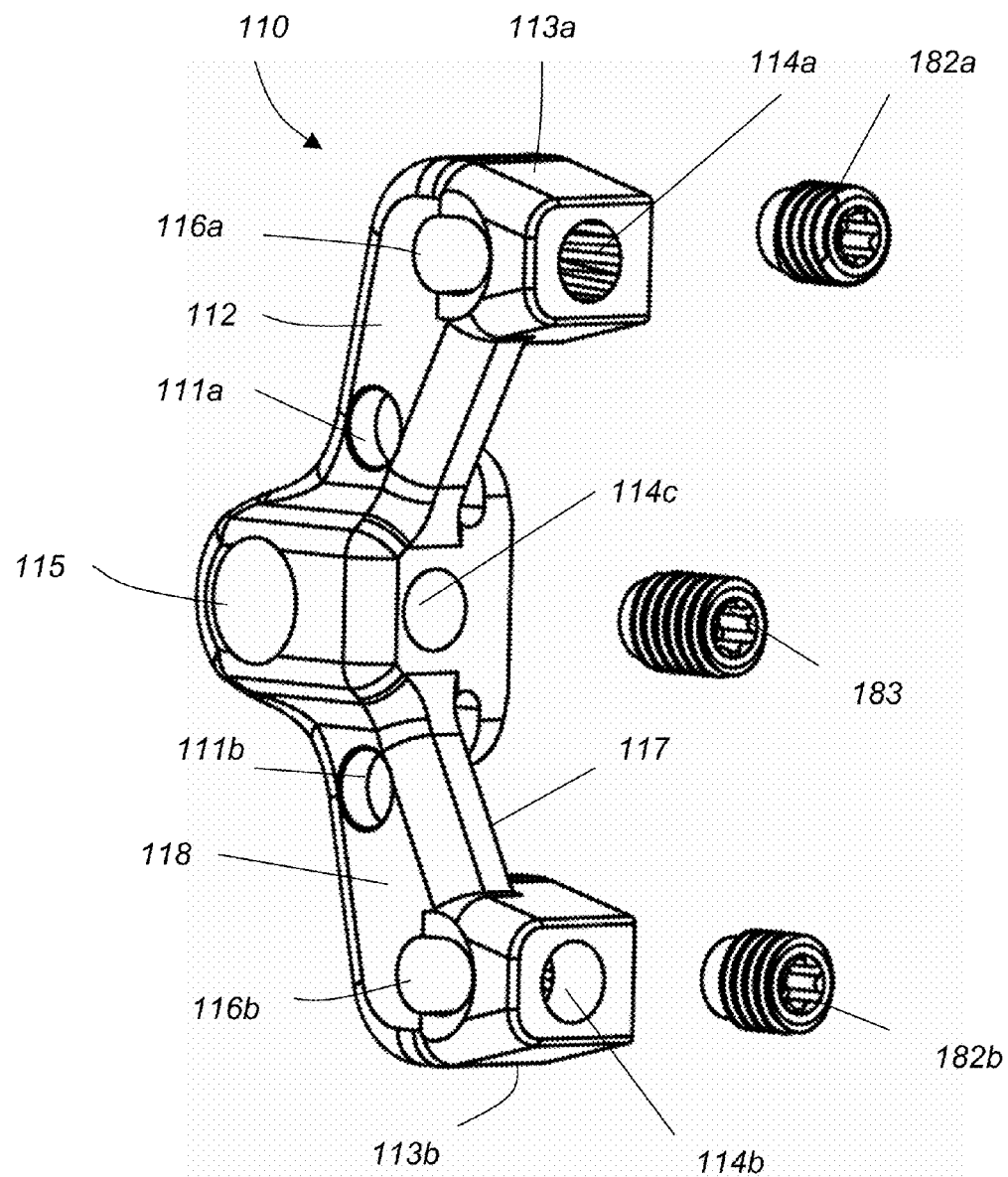
FIG. 5 is a left side perspective view of the elongated component 110 of the fixation implant of FIG. 2.

Referring to FIG. 5, elongated component 110 includes a body 112 having a top end 113a, a bottom end 113b, left side 118 and right side 117. Top and bottom ends 113a, 113b include side openings 116a, 116b respectively, extending from the left side 118 through to the right side 117. Side openings 116a, 116b are dimensioned to receive pins 160a, 160b, respectively, shown in FIG. 3. Pins 160a, 160b pass through openings formed in the spinous processes 90a, 90b, respectively, and then pass through openings 122, 132 formed in the pivoting wing components 120, 130, respectively, shown in FIG. 6, thereby providing additional fixation of the spinous processes. A portion of the right side surfaces 117 of the top and bottom ends 113a, 113b includes protrusions 111 designed to frictionally attach onto the left sides of the spinous processes 90a, 90b, respectively. Top and bottom ends 113a, 113b also include front openings 114a, 114b respectively, dimensioned to receive post set screws 182a, 182b, for securing the positions of pins 160a, 160b in the side openings 116a, 116b, respectively. Component 110 also includes a center through side opening 115 extending through the center of body 112 from the left side 118 through to the right side 117. Center opening 115 is dimensioned to receive a center pin 150 connecting component 110 to pivoting wing components 120 and 130. A center post set screw 183 is threaded into front opening 114c having an axis perpendicular to the axis of side opening 115 and secures the position of center pin 150 into the opening 115. The medial-lateral position of component 110 relative to center pin 150 is adjusted by unlocking post set screw 183. Left side surface 118 also includes two partial openings 111a, 111b, used to anchor tools for picking up and placing component 110 between the spinous processes 90a, 90b. The front surface of the elongated component 110 also includes partial openings (depressions) 119a, 119b used to anchor tools for picking up and placing the component.

Figure 8A:
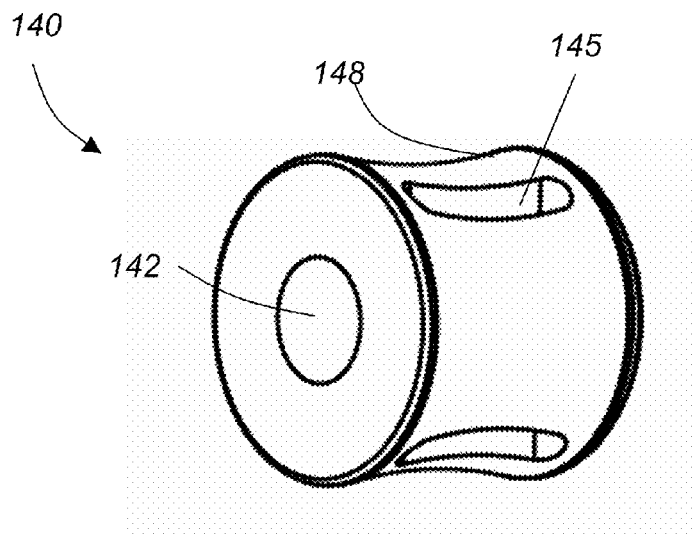
FIG. 8A is a perspective view of the spacer 140 of the fixation implant of FIG. 2.
Figure 8B:
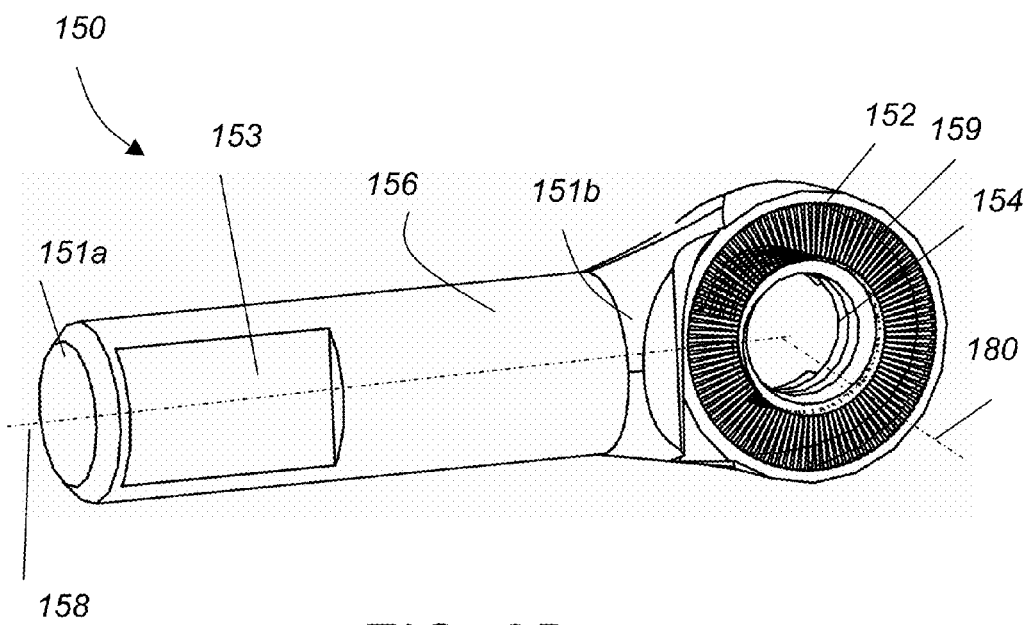
FIG. 8B is a perspective view of the center pin 150 of the fixation implant of FIG. 2.
Figure 9:
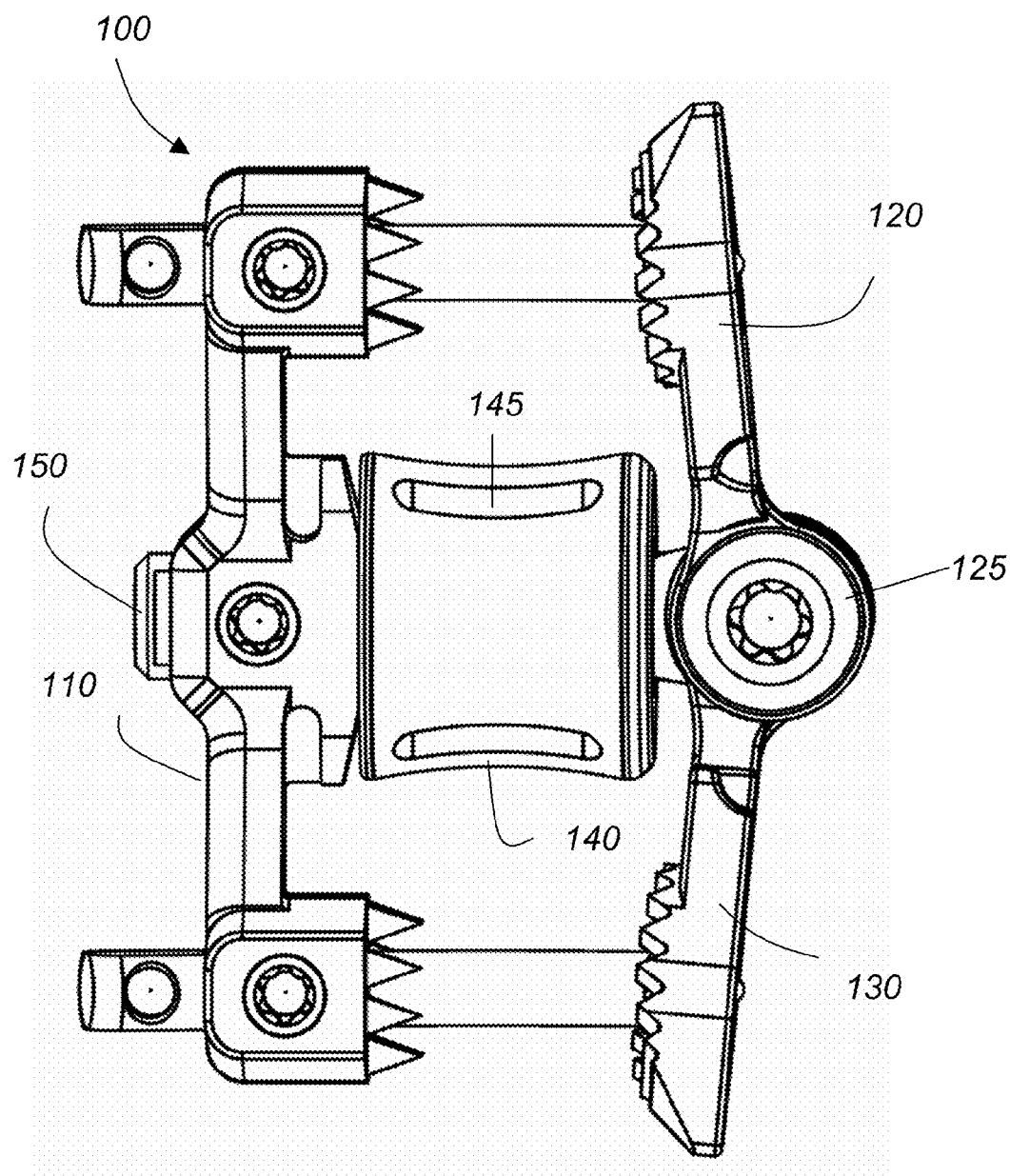
FIG. 9 is a front view of another embodiment of the spinous process fixation implant.

Referring to FIG. 8B, center pin 150 includes a cylindrical body 156 having a first end 151a protruding from the left side of opening 115 and a second end 151b having a ring 152 attached to it. Axis 180 of ring 152 is oriented perpendicular to the longitudinal axis 158 of the cylindrical body 156. Ring 152 includes inner threads 154 dimensioned to engage outer threads of a long bolt/locking hub 185, shown in FIG. 6. In some embodiments, the front surface of ring 152 includes grooves 159 designed to interlock with grooves 189 formed on the surfaces of rings 134 and 124 of the pivoting wing components, as will be described below. Cylindrical body 156 also includes a depression 153 for receiving the center post set screw 183. Cylindrical body 156 is dimensioned to pass through a center opening 142 of the spacer component 140, shown in FIG. 8A. Spacer 140 is placed between the spinous processes 90a, 90b and provides cephalocodal support of the spinous processes 90a, 90b. Spacer 140 is shaped and dimensioned to fit the geometry and local anatomy of the spinous processes. In one example, spacer 140 is cylindrically shaped and has a sculpted outer surface 148, as shown in FIG. 8A. In particular, spacer 140 has a curved outer surface and the diameter of the cylinder in the center section is smaller than the diameter of the cylinder at the ends. In some embodiments spacer 140 includes fenestrations 145, shown in FIG. 9. In other embodiments fenestrations 145 are filled with graft material. The graft material promotes bone growth and provides enhanced fusion. In some embodiments, spacer 140 and the other components of the assembly are coated with hydroxy-apatite coating to promote bone growth. In other embodiments, spacer 140 is fixedly attached to component 110 or is an extension of elongated component 110, as shown in FIG. 5A.

Figure 6:
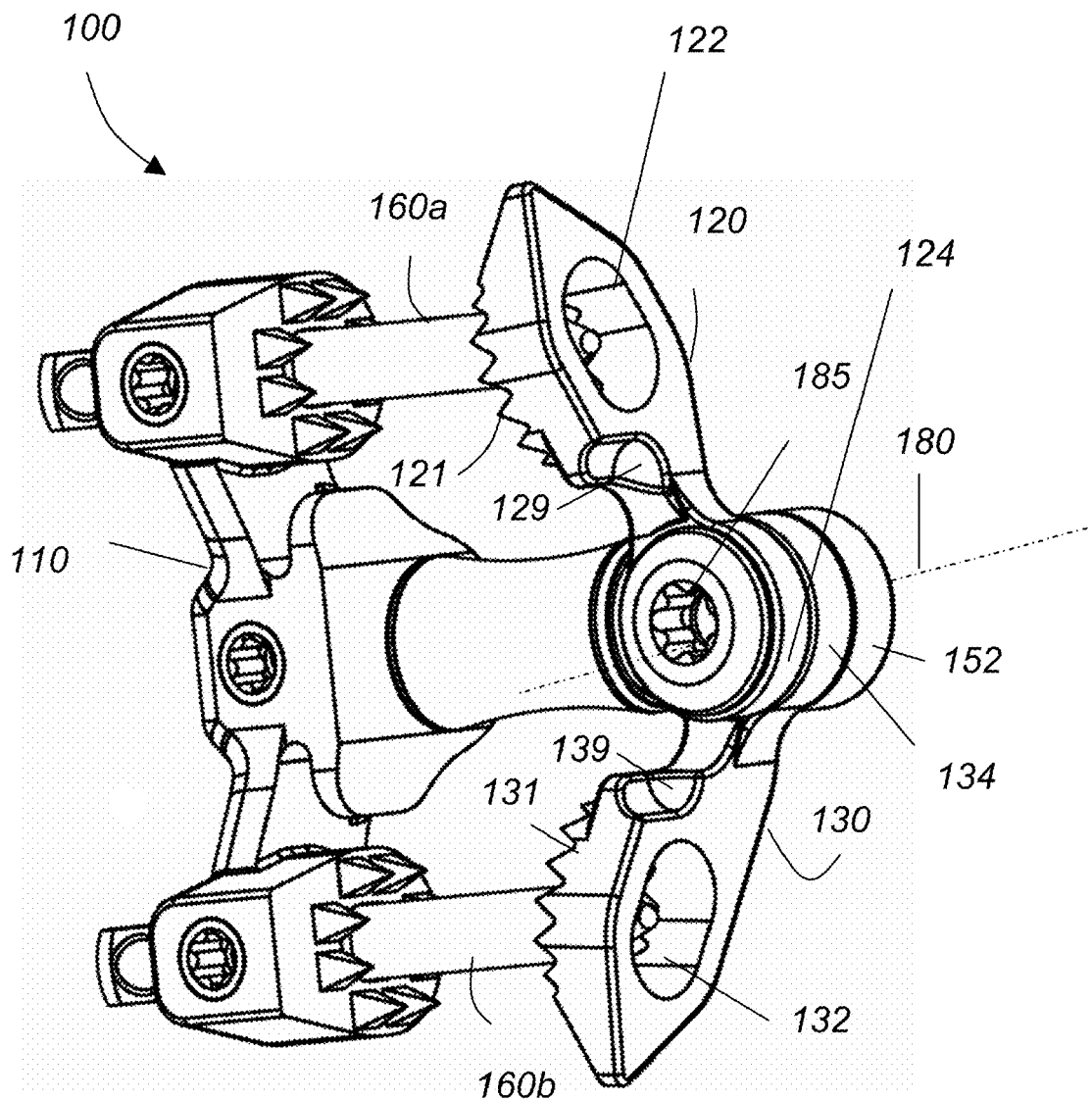
FIG. 6 is a perspective view of the spinous process implant of FIG. 2.
Figure 7:
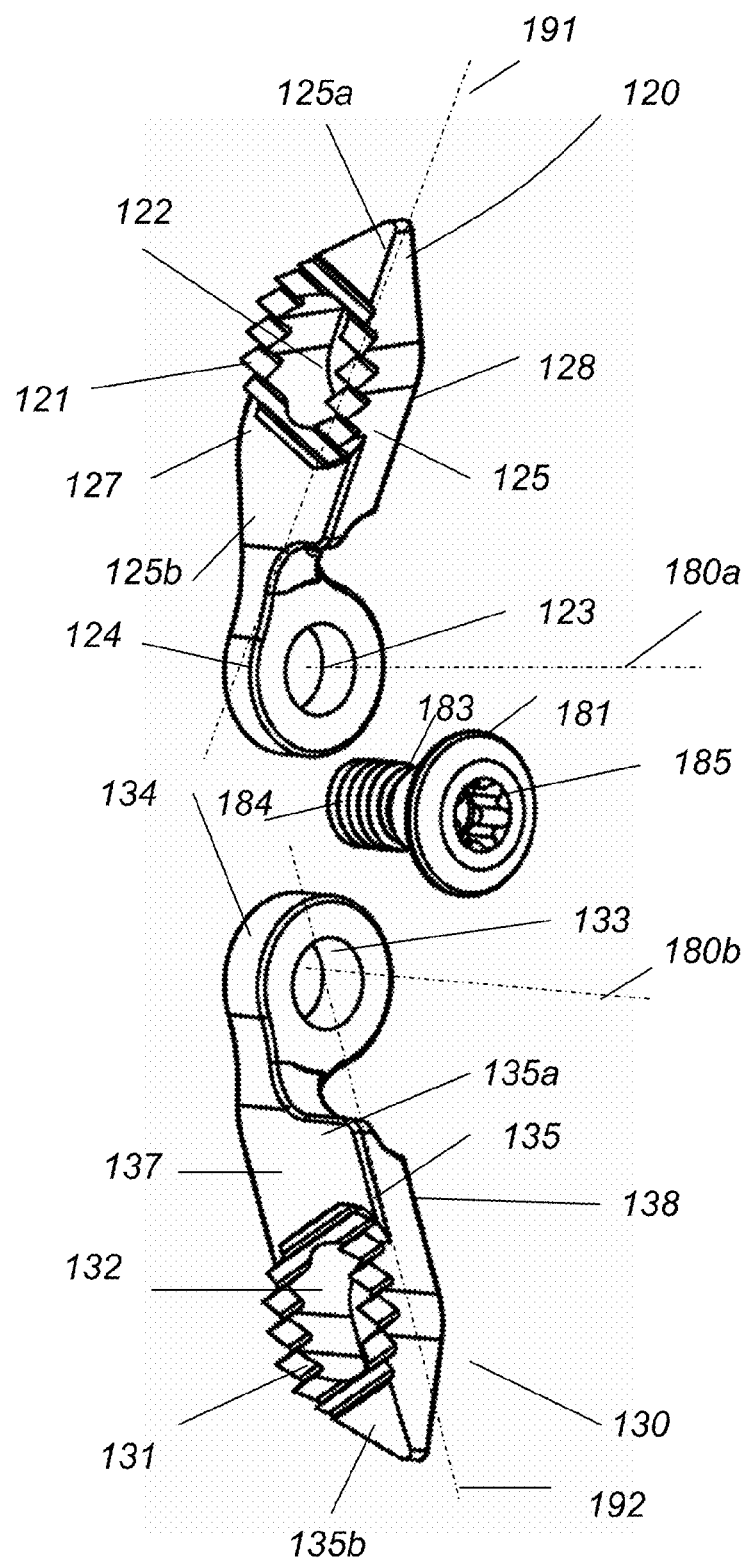
FIG. 7 is an exploded view of the pivoting wing components of the fixation implant of FIG. 2.
Figure 8C:
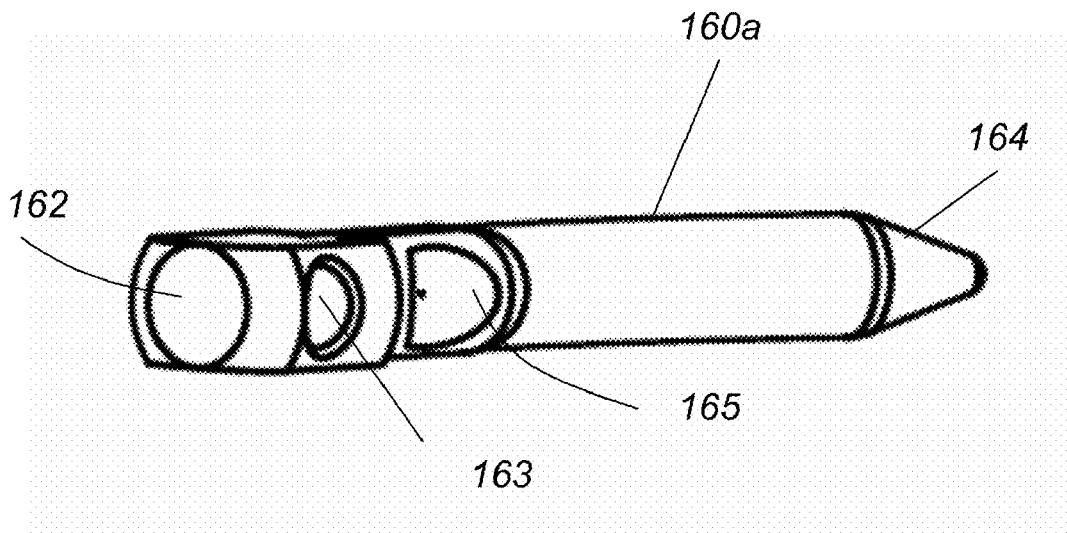
FIG. 8C is a perspective view of pin 160a of the fixation implant of FIG. 2.
Figure 7A:
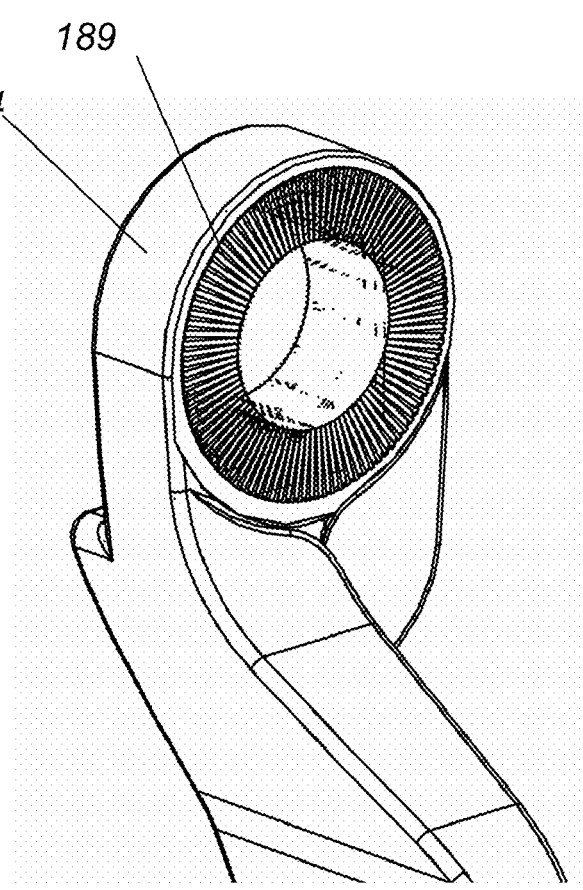
FIG. 7A is a detailed view of ring 134 of FIG. 7.

Referring to FIG. 7, top pivoting wing component 120 includes a main body 125 having top and bottom ends 125a, 125b, respectively, and left and right side surfaces 127, 128, respectively. A ring 124 extends downward from the bottom end 125b and has an axis 180a passing through opening 123 perpendicular to the main axis 191 of component 120. Top end 125a includes a through opening 122 extending from the left side to the right side of the component. Opening 122 is dimensioned to receive pin 160a, as shown in FIG. 6. Similarly, bottom pivoting wing component 130 has a main body 132 having top and bottom ends 135a, 135b, respectively, and left and right side surfaces 137, 138 respectively. A ring 134 extends upward form the top end 135a and has an axis 180b passing through opening 133 perpendicular to the main axis 192 of component 130. In some embodiments, the front surfaces of rings 124, 134 and the back surface of ring 124 include grooves 189 designed to interlock with grooves 159 formed in the front surface of ring 152, as shown in FIG. 7A. The interlocking of grooves 189 with grooves 159 provides an additional locking mechanism for the attachment of the pivoting wing components 120, 130 to the center pin 150. Bottom end 135b of pivoting wing component 130 includes a through opening 132 extending from the left side to the right side of the component. Opening 132 is dimensioned to receive pin 160b, as shown in FIG. 6. Surfaces 128 and 138 of components 120, 130, include partial openings (depressions) 129, 139 used to anchor tools for picking up and pivoting components 120, 130, respectively, shown in FIG. 6. Components 110, 120, 130 are made of stainless steel, titanium, gold, silver, alloys thereof, or absorbable material and may adjustable lengths.

Referring to FIG. 6, long bolt/locking hub 185 passes through aligned apertures 123, 133 of the top and bottom pivoting wing components 120, 130, respectively, and is threaded into aperture 154 of the center pin ring 152. Bolt 185 has a head 181, a shaft 183 and outer threads 184 formed on the end portion of the shaft 183. Outer threads 184 engage inner threads in aperture 154 of the center pin ring 152, in order to hold and secure the three components 120, 130 and 150 of the assembly 100 together. In other embodiments, a nut (not shown) is attached at the end of the bolt 185 to hold and secure the three components 120, 130 and 150 of the assembly 100 together. In other embodiments bolt 185 is threaded into the cartilage between the two vertebras to secure components 110, 120, 150 together and to attach the assembly 100 onto the spine. Portions of inner surfaces 117, 127, 137 of components 110, 120, 130, respectively, have protrusions 111, 121, 131, respectively, that grab and frictionally engage the sides of the spinous processes 90a, 90b, as shown in FIG. 2. Protrusions 111 may be teeth, serrations, ridges, and other forms of rough surfaces or coatings that produce rough surfaces. The position of pivoting wing components 120, 130 relative to each other and relative to component 110 is locked with the long bolt 185. Engaging and locking the spinous process fixation assembly 100 onto spinous processes 90a, 90b, prevents the components 110, 120 and 130 from moving sidewise or up and down toward or away from each other during spinal movement.

Figure 20A:
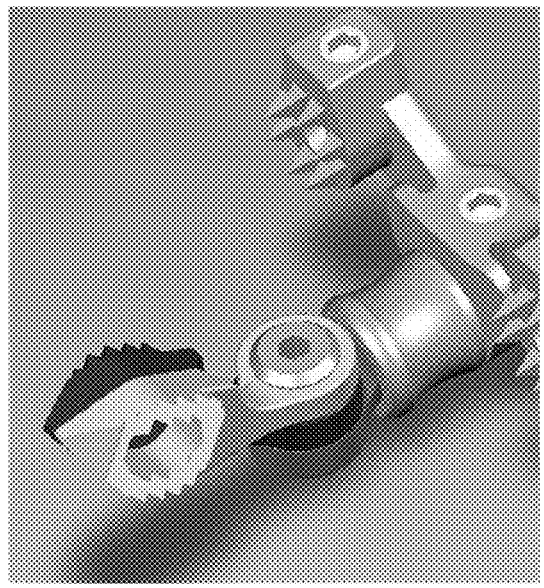
FIG. 20A depicts the fixation device of FIG. 2 with the wing components collapsed.
Figure 20B:
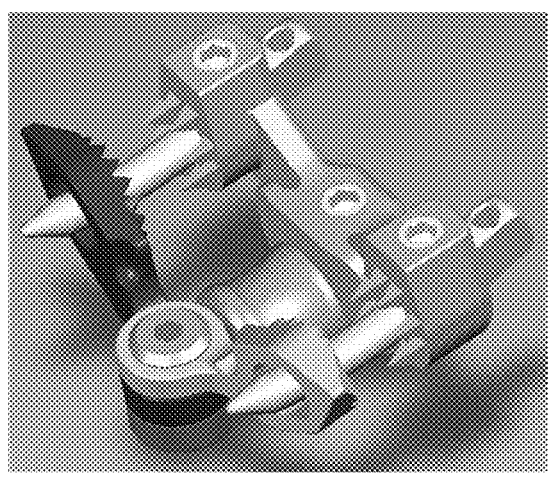
FIG. 20B depicts the fixation device of FIG. 2 with the wing components spread.
Figure 21:
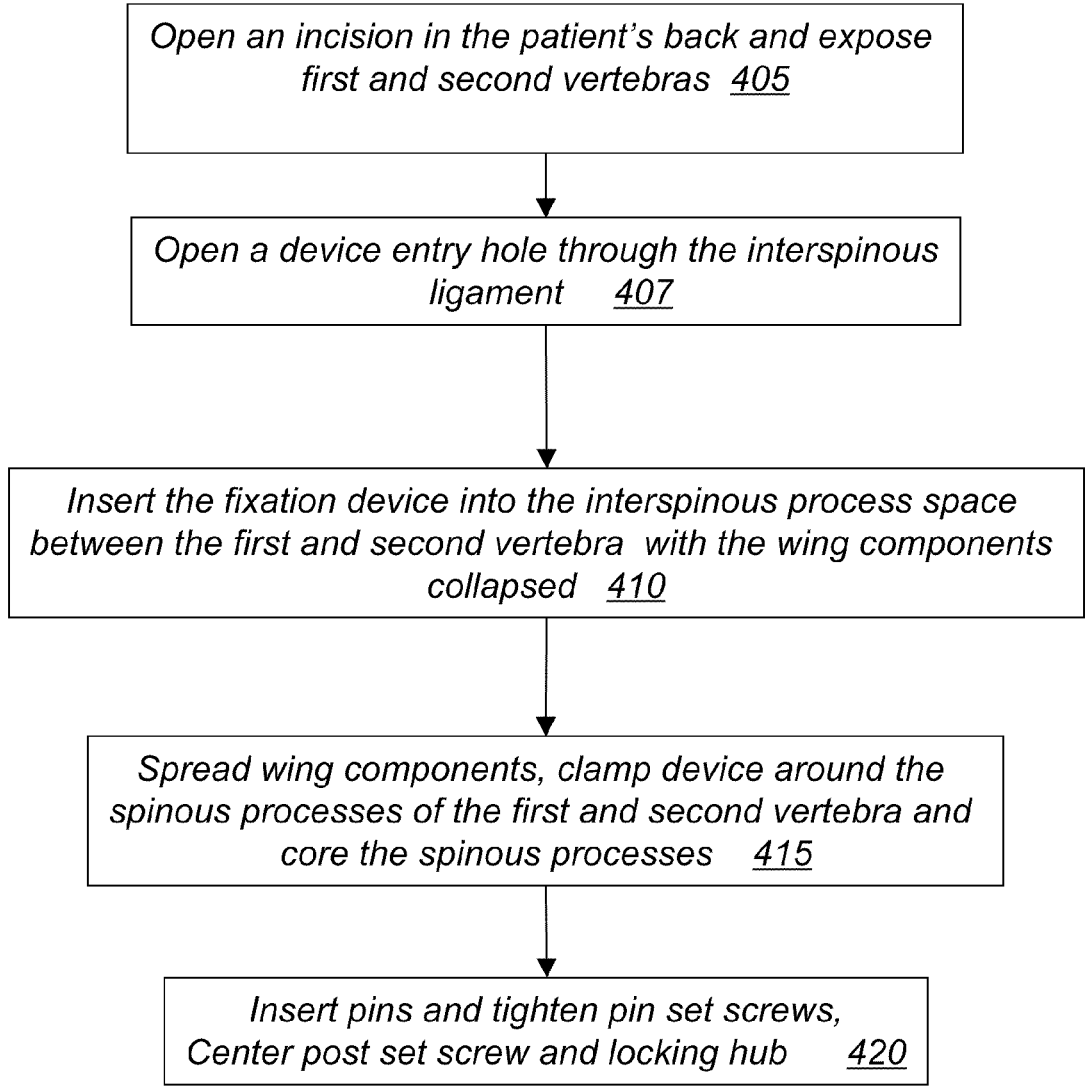
FIG. 21 depicts the method of implanting the fixation device of FIG. 2.

The assembled spinous process fixation assembly 100 is implanted into the patient with the use of instrumentation between the two adjacent spinous processes 90a, 90b, as shown in FIG. 2. Referring to FIG. 21, the implantation process 400 includes the following steps. First, the surgeon makes an incision in the patient's back and exposes the first and second vertebras, 92, 94 (405). Next a dilator 300 (shown in FIG. 10) is used to open a device entry hole through the interspinous ligament (407). Next, the surgeon uses an inserter tool 310 (shown in FIG. 11) to grasp and insert the device into the interspinous process space between the first and second vertebras 92, 94 with the wing components 120, 130 collapsed (as shown in FIG. 20A) (410). The spacer 140 is placed between the spinous processes 90a, 90b so that the body 112 of the elongated component 110 and the top and bottom pivoting wing components 120, 130 fall on the lateral sides of the spinous processes 90a, 90b. One spinous process 90a lies between the top portion 113a of the body 112 and the top pivoting wing component 120 and the other spinous process 90b lies between the bottom portion 113b of the body 112 and the bottom pivoting wing component 130, with their inner surfaces 117, 127, 137 facing the lateral surfaces of the spinous processes 90a, 90b. On each of the inner surfaces 117, 127, 137 of the components 110, 120, 130, respectively, the protrusions 111, 121, 131 face toward the lateral surface of the adjacent spinous process. Next, the wing components 120, 130 are spread with the wing spreader 330 (shown in FIG. 13), the spinous processes 90a, 90b are clamped between the top 113a and bottom 113b of the elongated component 110 and the wing components 120 and 130, respectively, and then the spinous processes 90a, 90b are cored with the trocar-tipped cortical punch of FIG. 18 (415). Next, the top and bottom pins 160a, 160b, are inserted, the pin set screws 182a, 182b are tightened and the center post set screw 183 and locking hub 185 are tightened (420). The tightening of the set screws 182a, 182b, 183 and of the locking hub 185, clamps the protrusions 111, 121, 131 into the surfaces of the spinous processes, locks the three components relative to each other and frictionally secures the spinous process fixation assembly 100 onto the spinous processes 90a, 90b and helps prevent the device from shifting or slipping.

Figure 10:
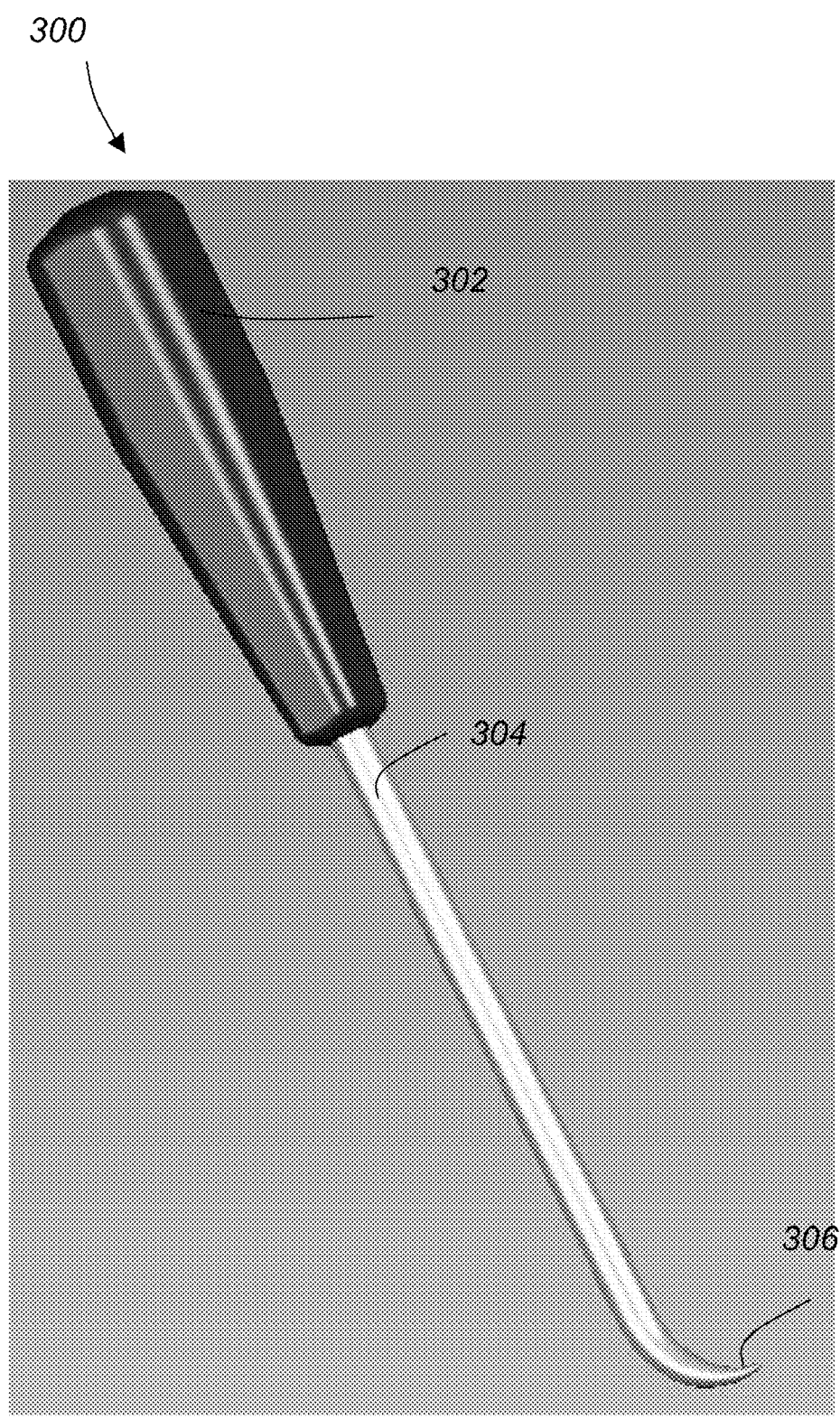
FIG. 10 is a perspective view of a dilator tool.

Referring to FIG. 10, dilator 300 includes an elongated body 304 having a handle 302 at one end and a sharp curved tip 306 at the opposite end. The curved tip end is used to create entry holes through the interspinous ligament without affecting the surrounding anatomy.

Figure 11:
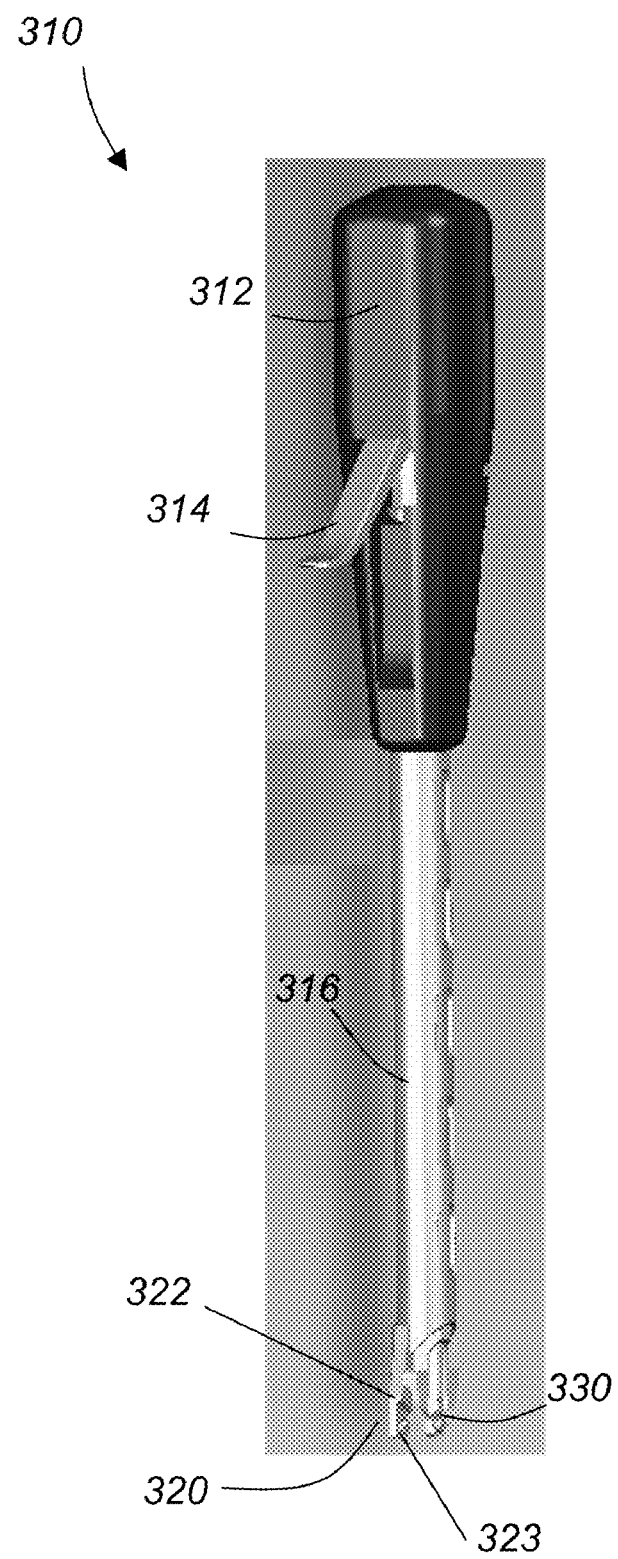
FIG. 11 is a perspective view of an inserter tool.
Figure 12:
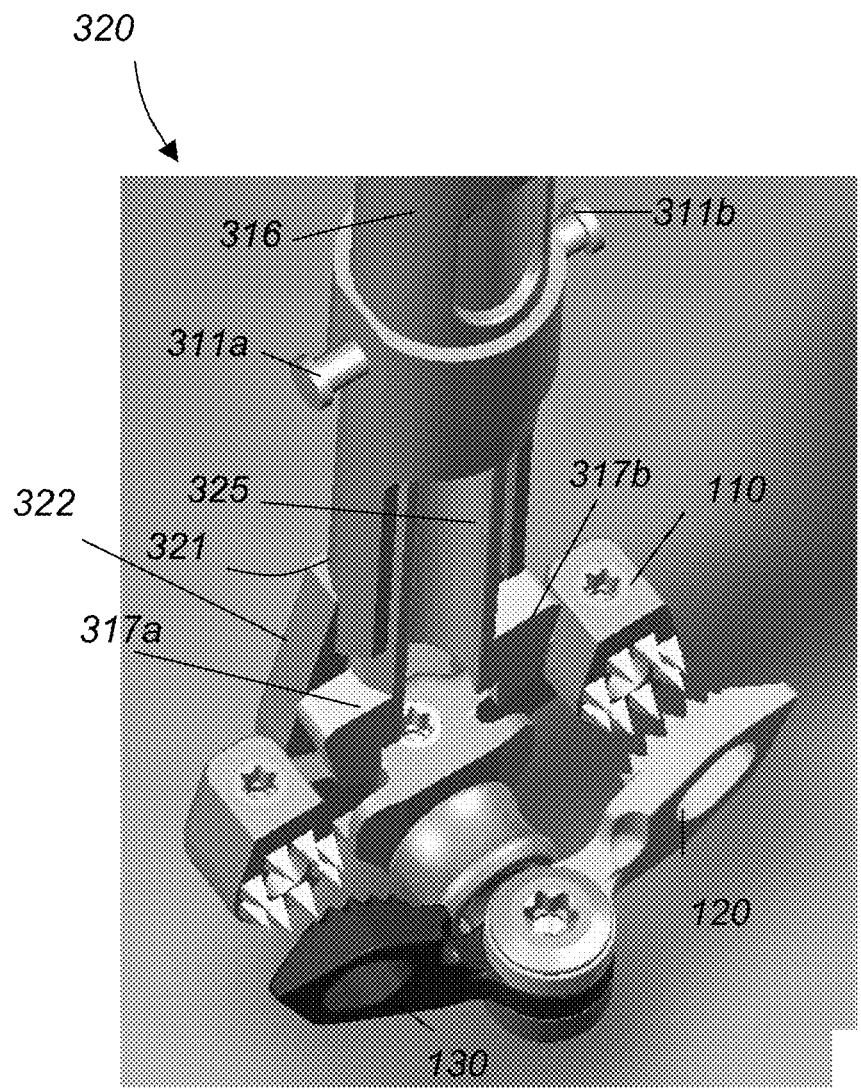
FIG. 12 is a detailed view of a grasper attachment used in connection with the inserter tool of FIG. 11.

Referring to FIG. 11, inserter 310 includes an elongated tubular body 316, a handle 312 disposed at the proximal end of the body 316 and a grasper 320 disposed at the distal end of the tubular body 316. Handle 312 includes a lever 314 used to actuate capturing or releasing of a component via the grasper 320. Referring to FIG. 12, grasper 320 includes an outer tubular component 321 and an inner tubular component 325. Inner tubular component 325 is disposed within the tubular body 316 and outer tubular component 321 is an extension of the tubular body 316. Outer tubular component 321 includes a grasping element 322 having pins 323a, 323b. Pins 323a, 323b are configured to be inserted into partial holes 111a, 111b of the elongated component 110 during the grasping action. Inner tubular component 325 includes two spread out grasping elements 317a, 317b. Grasping elements 317a, 317b are configured to be spaced apart and to be inserted into partial openings (depressions) 119a, 119b of the elongated body 110 for picking up and placing the entire fixation device 100. Grasping elements 317a, 317b are actuated via lever 314. Tubular body 316 also includes pins 311a, 311b used to engage clamps 380 and other attachments, shown in FIG. 15.

Figure 13:
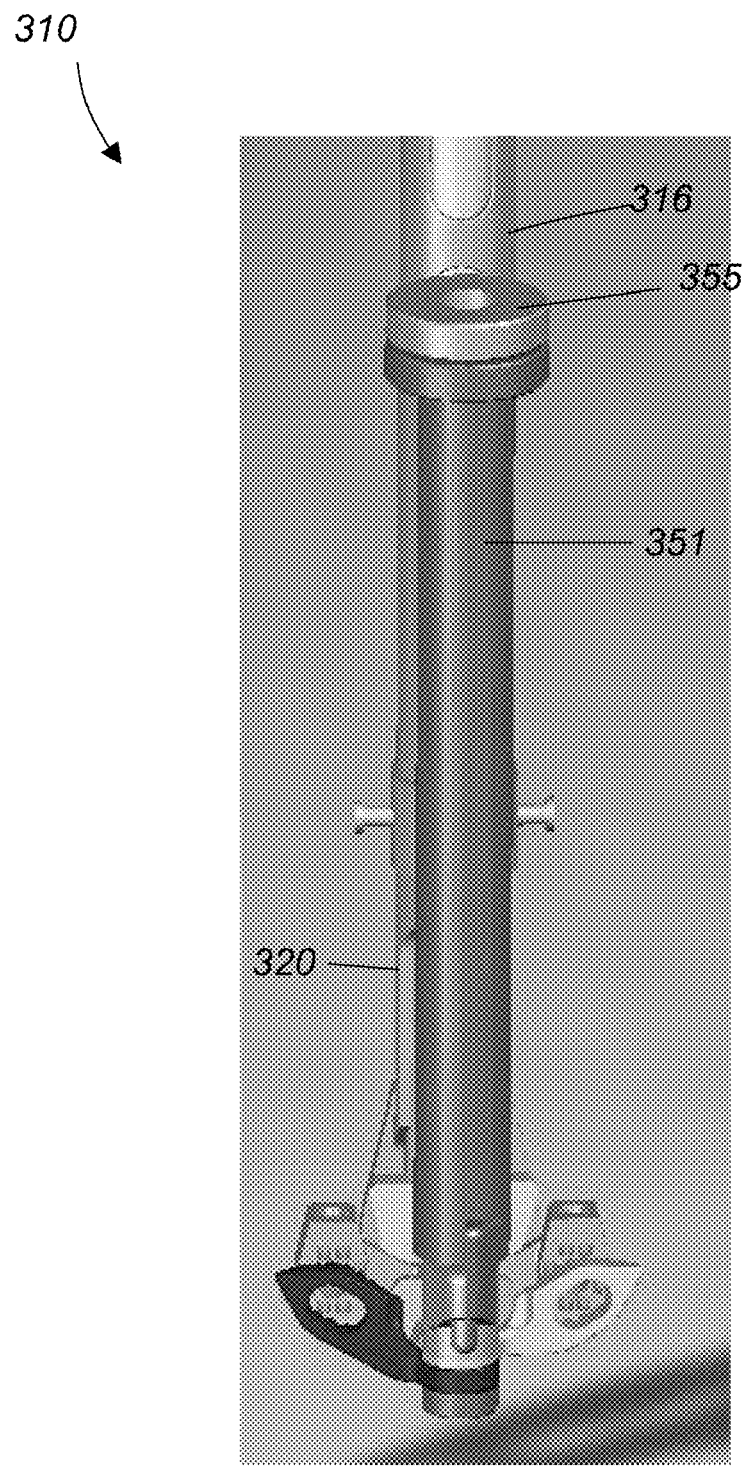
FIG. 13 is a perspective view of a wing spreader tool.
Figure 14A:
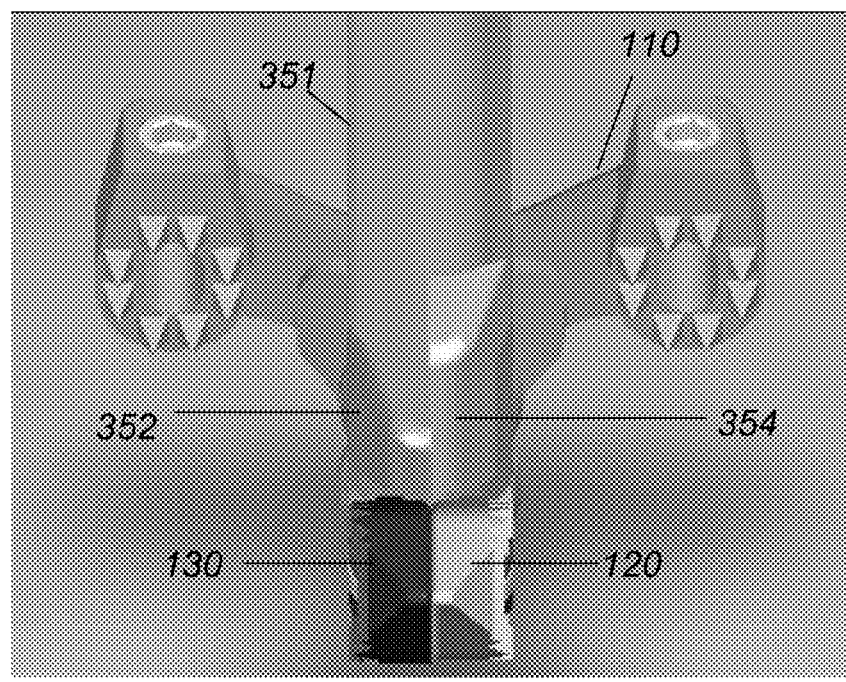
FIG. 14A is a detailed view of the wing spreader tool of FIG. 13 in the closed position.
Figure 14B:
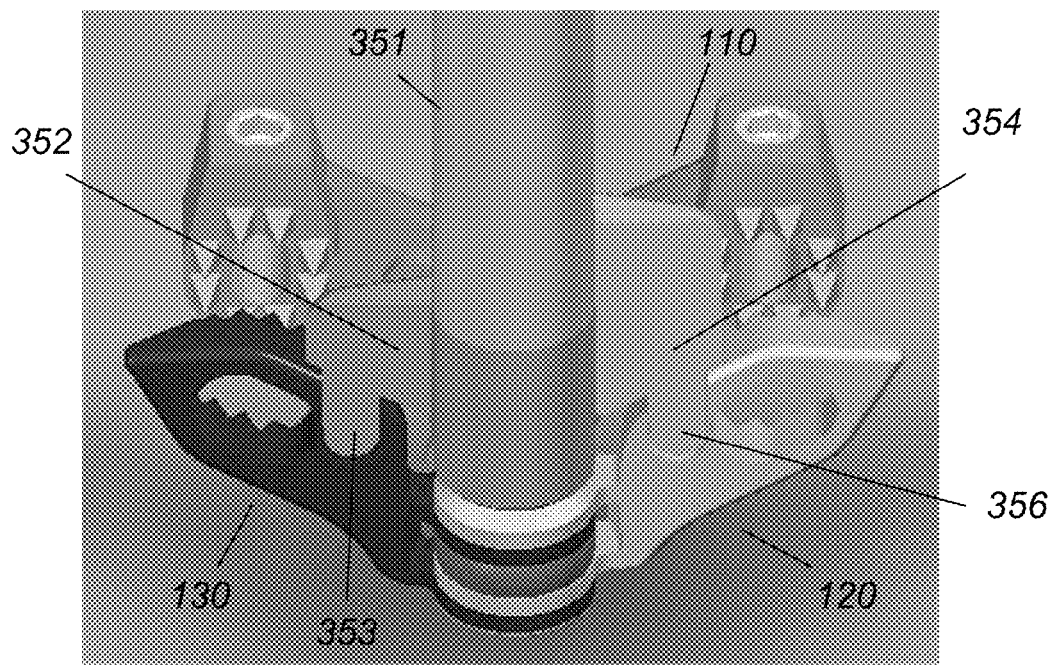
FIG. 14B is a detailed view of the wing spreader tool of FIG. 13 in the open position.

Referring to FIG. 14A and FIG. 14B a wing spreader 350 includes an outer tubular body 351 having a handle at the proximal end (not shown) and terminating into first spreading element 354. Wing spreader 350 also includes an inner tubular body 355 disposed within outer tubular body 351 and terminating at a second spreading element 352. In other embodiments, wing spreader 350 is an attachment that is attached to the side of the tubular component 316 of the inserter 310, as shown in FIG. 13. In operation, tubular body 351 is placed over the locking hub 185, the spreading elements 352, 354 engage the wing components 130, 120, respectively, and open or close them. Spreading elements 352, 354 include projections 353, 356, respectively. Projections 353, 356 are configured to be inserted into partial openings (depressions) 129, 139, formed on surfaces 128 and 138 of components 120, 130, respectively. Spreading elements 352, 354 are configured to be pivoted independent from each other via separate actuator causing the inner and outer tubular bodies 355, 351 to rotate. A screwdriver is inserted through the inner tubular body 355 for tightening the locking hub 185.

Figure 15:
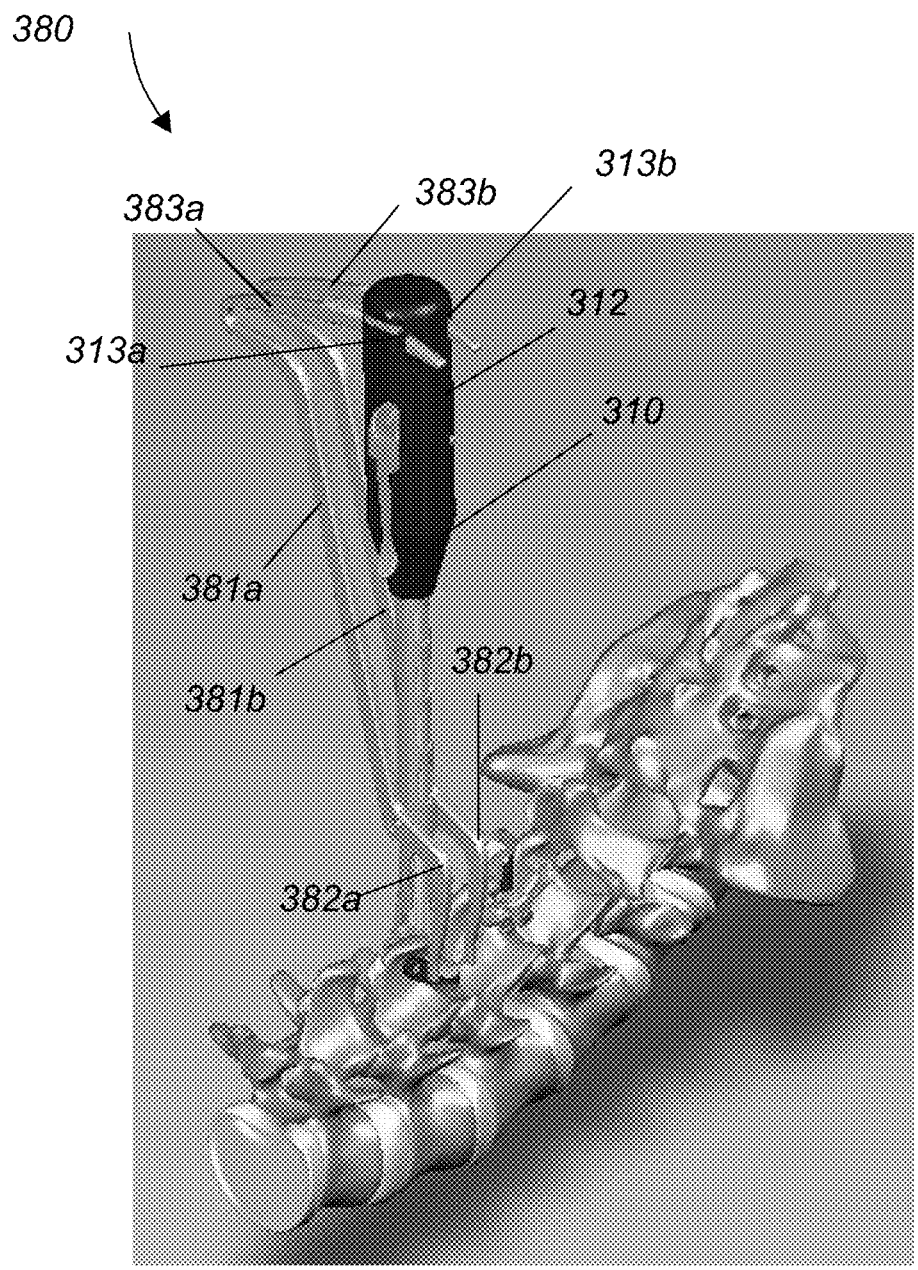
FIG. 15 is a perspective view of a clamps assembly used in connection with the inserter tool of FIG. 11.
Figure 16:
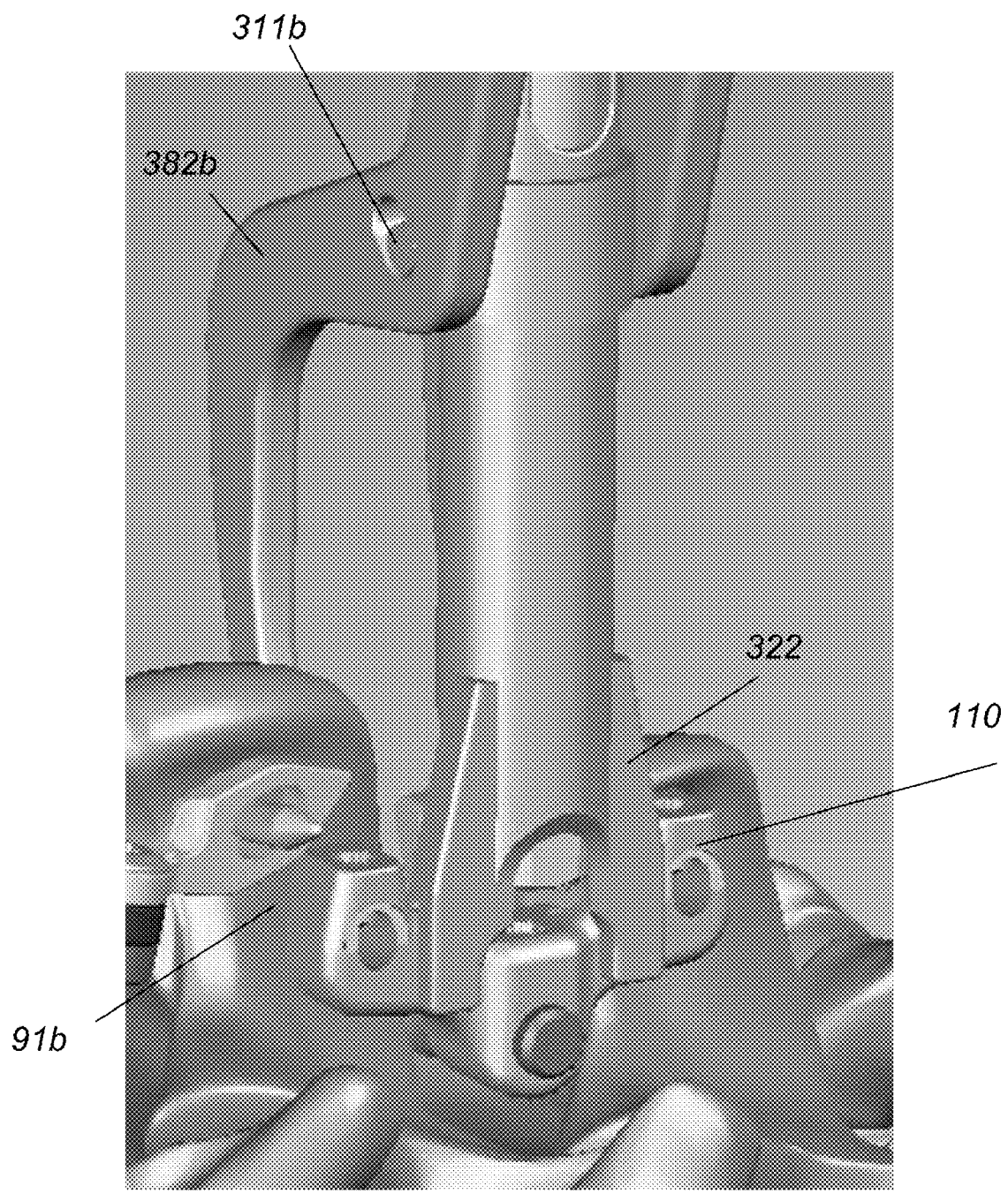
FIG. 16 and FIG. 17 are detailed views of the clamps attachment of FIG. 15.
Figure 17:
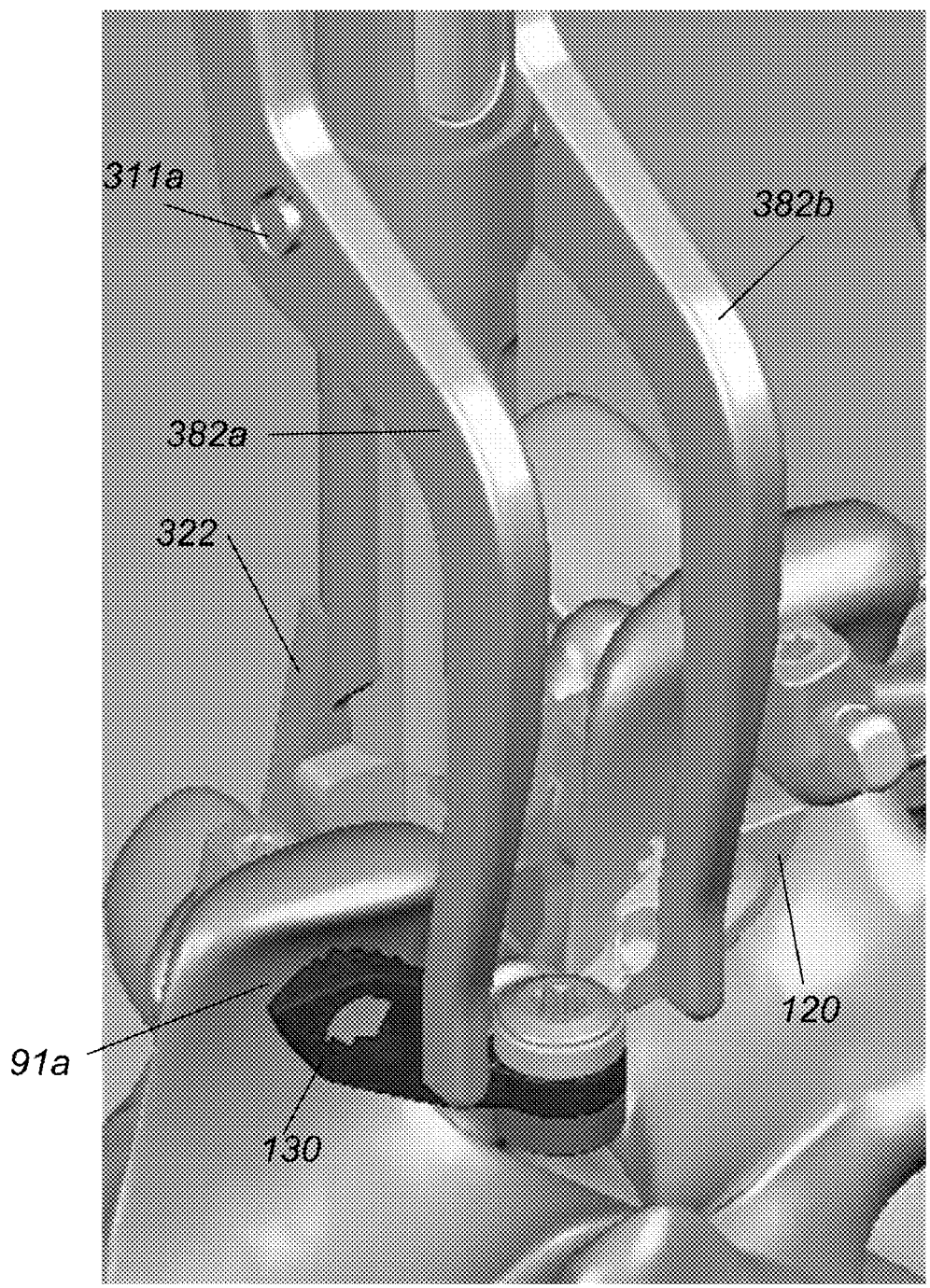

Referring to FIG. 15, clamps 380 assemble easily to the inserter 310 by engaging pins 311a, 311b of the tubular body 316. Clamps 380 hold the fixation device 100 in place and press the wing components 120, 130 against the first lateral surfaces 91a of the spinous processes, while the grasping element 322 of the inserter 310 presses the elongated component 110 against the opposite lateral surfaces 91b of the spinous processes, as shown in FIG. 17 and FIG. 16. Clamps 380 include first and second parallel arranged clamping elements 381a, 381b, terminating into prongs 382a, 382b. The proximal ends of the clamping elements include handles 383a, 383b that engaged loops 313a, 313b formed in the handle 312 of the inserter 310.

Figure 18:
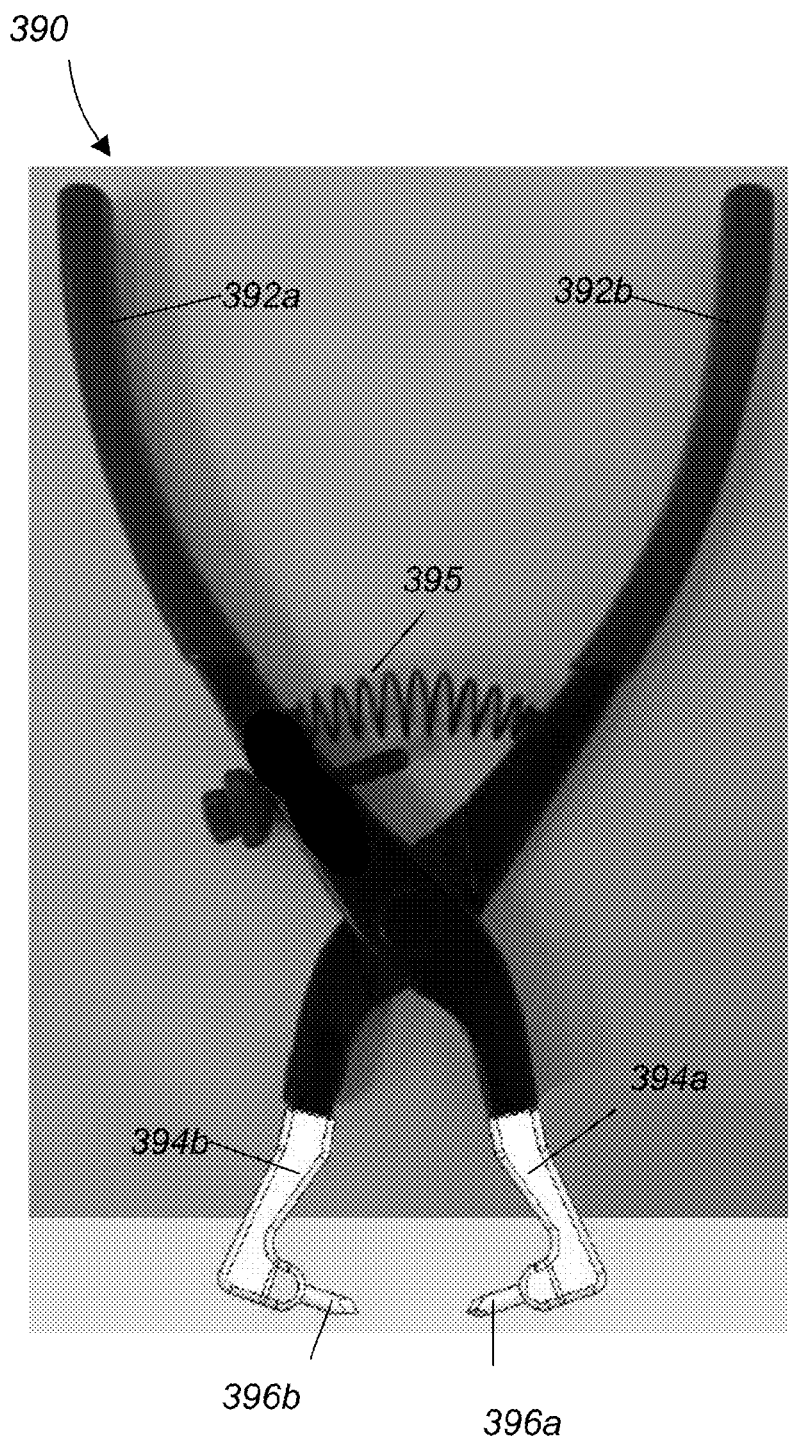
FIG. 18 is a schematic view of the trocar-tipped cortical punch tool.
Figure 19:
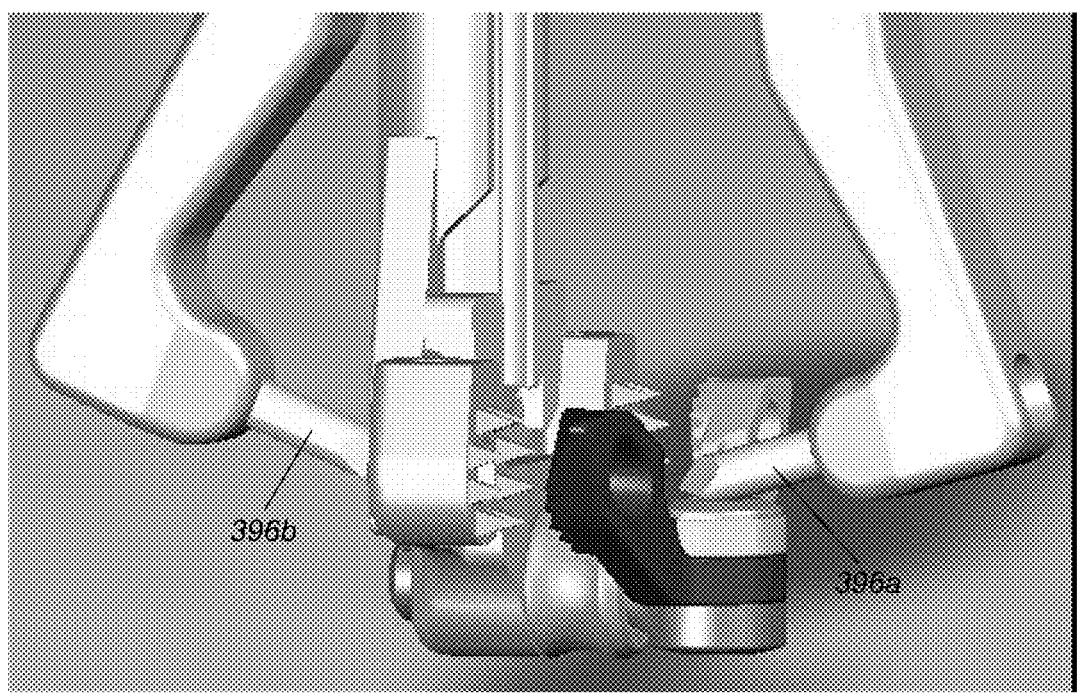
FIG. 19 is a detailed view of the trocar-tipped cortical punch tool.

Referring to FIG. 18 a trocar-tipped cortical punch 390 includes disposable tips 396a, 396b at the end of the prongs 394a, 394b. The disposable tips 396a, 396b are used to start the pin holes through the cortical bone of the spinous process simultaneously on both sides 91a, 91b of the spinous process, as shown in FIG. 19. Once the holes are punched through the spinous processes, pins 160a, 160b are inserted through the top 113a and bottom 113b portions of the elongated component 110, the spinous processes and the wing components 120, 130. In other embodiments cortical punch 390 includes one tip 396a and the end of prong 394a and an opening at the end of prong 394b (not shown). The opening at the end of prong 394b is dimensioned to receive tip 396a, when the prongs 394a, 394b are closed.

Other embodiments are within the scope of the following claims. For example, vertebras 92 and 94 may be any two vertebras, including lumbar L1-L5, thoracic T1-T12, cervical C1-C7 or the sacrum. The fixation assembly 100 may extend along multiple vertebras. The fixation assembly 100 of FIG. 3 may be also configured as a mirror image of the structure in FIG. 3, with the pivoting wing components 120, 130 located on the left side and the elongated component 110 located on the right side of the FIG. 3. The elongated component 110, and the top and bottom pivoting wing components 120, and 130, respectively, may have adjustable lengths. Elongated component 110 and spacer 140 may be incorporated into one component or may be fixedly attached to each other. Center post set screw 183 may be also used to secure component 110 onto a location of either vertebra 92, 94. Pins 160a, 160b may not be included in the assembly 100. Spacer 140 may not be a separate component. Spacer 140 may be an integral part of body 156. Spacer 140 may have straight (non-curved) outer surface 148.

Several embodiments of the present invention have been described. Nevertheless, it will be understood that various modifications may be made without departing from the spirit and scope of the invention. Accordingly, other embodiments are within the scope of the following claims.

What is claimed is:

1. An implantable assembly for stabilization of two adjacent spinous processes in a spinal column, comprising:
   an elongated component extending along a first axis;
   a first pivoting wing;
   a second pivoting wing;
   a spacer extending along a second axis, wherein said second axis is perpendicular to said first axis and wherein said spacer is placed between said elongated component and said first and second pivoting wings;
   a central pin dimensioned to pass through two concentrically aligned through-bore openings formed in said spacer along said second axis and in the center of said elongate component, respectively, and wherein said central pin comprises a ring extending from a first end and wherein said ring defines a through opening extending along a third axis;
   wherein said first and second pivoting wings are arranged opposite to said elongated component at a distance defined by said spacer width and comprise inner surfaces that face an inner surface of said elongated component;
   wherein said first and second pivoting wings pivot around said third axis, wherein said third axis is perpendicular to said first axis and said second axis; and
   wherein a first spinous process is placed and clamped between said first pivoting wing inner surface and a first area of said elongated component inner surface by pivoting said first pivoting wing toward said elongated component and a second spinous process is placed and clamped between said second pivoting wing inner surface and a second area of said elongated component inner surface by pivoting said second pivoting wing toward said elongated component.

2. The assembly of claim 1 further comprising first and second pins and wherein said first pin is dimensioned to pass through three concentrically aligned through-bore openings formed in said first pivoting wing, said first spinous process and said first area of said elongated component, respectively, and wherein said second pin is dimensioned to pass through three concentrically aligned through-bore openings formed in said second pivoting wing, said second spinous process and said second area of said elongated component, respectively.

3. The assembly of claim 1 wherein said first and second areas of said elongated component inner surface and said first and second wing inner surfaces comprise protrusions designed to frictionally attach to surfaces of said first and second spinous processes, respectively.

4. The assembly of claim 3 further comprising first, second and third locking elements for securing said first, second and central pins, respectively, to said elongated component and wherein said locking elements comprise a set screw dimensioned to engage threads formed in openings formed in said elongated component, and wherein said openings extend along an axis perpendicular to said first and second axes.

5. The assembly of claim 1 wherein each of said pivoting wings comprise a ring extending from a first end of each pivoting wing and wherein said pivoting wing rings are oriented and placed concentric with said central pin ring along said third axis.

6. The assembly of claim 5 further comprising an elongated bolt dimensioned to pass through said pivoting wing rings and said central pin ring and wherein said elongated bolt comprises threads formed at a portion of said bolt, and said threads are dimensioned to engage a nut after the bolt exits said rings.

7. The assembly of claim 5 wherein said central pin ring comprises radially extending grooves that interlock with radially extending grooves formed in said pivoting wing rings.

8. The assembly of claim 1, wherein said spacer is dimensioned to fit between said first and second spinous processes and comprises an outer surface that is sculpted to conform to the shape of said spinous processes.

9. The assembly of claim 1 wherein said spacer comprises fenestrations configured to receive bone growth promoting material.

10. The assembly of claim 1 wherein said spacer is an integral extension of said elongated component.

11. A method for stabilizing two adjacent spinous processes in a spinal column, comprising:
   providing an elongated component extending along a first axis;
   providing a first pivoting wing;
   providing a second pivoting wing;
   providing a spacer extending along a second axis, wherein said second axis is perpendicular to said first axis;
   providing a central pin dimensioned to pass through two concentrically aligned through-bore openings formed in said spacer along said second axis and in the center of said elongate component, respectively, and wherein said central pin comprises a ring extending from a first end and wherein said ring defines a through opening extending along a third axis;
   placing said spacer between said elongated component and said first and second pivoting wings;
   arranging said first and second pivoting wings opposite to said elongated component and placing them at a distance defined by said spacer width so that inner surfaces of said pivoting wings face an inner surface of said elongated component;
   pivoting said first and second pivoting wings around said third axis, wherein said third axis is perpendicular to said first axis and said second axis;
   placing a first spinous process and clamping it between said first pivoting wing inner surface and a first area of said elongated component inner surface; and
   placing a second spinous process and clamping it between said second pivoting wing inner surface and a second area of said elongated component inner surface.

12. The method of claim 11 further comprising providing first and second pins, and passing said first pin through three concentrically aligned through-bore openings formed in said first pivoting wing, said first spinous process and said first area of said elongated component, respectively, and passing said second pin through three concentrically aligned through-bore openings formed in said second pivoting wing, said second spinous process and said second area of said elongated component, respectively.

13. The method of claim 12 wherein said first and second areas of said elongated component inner surface and said first and second wing inner surfaces comprise protrusions designed to frictionally attach to surfaces of said first and second spinous processes, respectively.

14. The method of claim 11 wherein each of said pivoting wings comprise a ring extending from a first end of each pivoting wing and wherein said pivoting wing rings are oriented concentric with said central pin ring along said third axis.

15. The method of claim 14 further comprising providing an elongated bolt and passing it through said pivoting wing rings and said central pin ring and wherein said elongated bolt comprises threads formed at a portion of said bolt, and said threads are dimensioned to engage a nut after the bolt exits said rings.

16. The method of claim 11, wherein said spacer is dimensioned to fit between said first and second spinous processes and comprises an outer surface that is sculpted to conform to the shape of said spinous processes.

17. The method of claim 16 further comprising providing first, second and third locking elements for securing said first, second and central pins, respectively, to said elongated component and wherein said locking elements comprises a set screw dimensioned to engage threads formed in openings formed in said elongated component, wherein said openings extend along an axis perpendicular to said first and second axes.

* * * * *